United States Patent
Lingenfelder et al.

(10) Patent No.: US 9,498,547 B2
(45) Date of Patent: Nov. 22, 2016

(54) DYE SOLUTION

(75) Inventors: Christian Lingenfelder, Ulm (DE); Bastian Theisinger, Mannheim (DE); Wilfried Hiebl, Illerstissen (DE); Nadine Hagedorn, Blaustein (DE)

(73) Assignee: Fluoron GMBH, Ulm (DE)

( * ) Notice: Subject to any disclaimer, the term of this patent is extended or adjusted under 35 U.S.C. 154(b) by 380 days.

(21) Appl. No.: 12/990,427

(22) PCT Filed: Dec. 18, 2009

(86) PCT No.: PCT/EP2009/009144
§ 371 (c)(1),
(2), (4) Date: Dec. 14, 2010

(87) PCT Pub. No.: WO2010/078942
PCT Pub. Date: Jul. 15, 2010

(65) Prior Publication Data
US 2011/0190728 A1    Aug. 4, 2011

(30) Foreign Application Priority Data
Dec. 19, 2008    (DE) .................. 10 2008 064 065

(51) Int. Cl.
*A61K 31/74* (2006.01)
*A61K 49/00* (2006.01)
*A61F 9/00* (2006.01)

(52) U.S. Cl.
CPC ............... *A61K 49/006* (2013.01); *A61F 9/00* (2013.01)

(58) Field of Classification Search
CPC .................. A61K 9/0048; A61K 9/08; A61K 47/00; A61K 47/02; A61K 47/08; A61K 47/36
USPC ............................... 424/78.04, 9.1; 604/521
See application file for complete search history.

(56) References Cited

U.S. PATENT DOCUMENTS

| | | | | |
|---|---|---|---|---|
| 3,843,782 | A * | 10/1974 | Krezanoski et al. | 424/677 |
| 3,947,573 | A * | 3/1976 | Rankin | C08L 71/02 424/78.04 |
| 6,692,526 | B1 | 2/2004 | Snyder et al. | |
| 6,696,430 | B1 * | 2/2004 | Melles | A61K 49/006 424/9.6 |
| 6,802,829 | B2 | 10/2004 | Buono | |
| 7,014,991 | B2 | 3/2006 | Buono | |
| 2003/0060763 | A1 * | 3/2003 | Penfold et al. | 604/116 |
| 2003/0096334 | A1 | 5/2003 | Buono | |
| 2005/0202097 | A1 * | 9/2005 | Maskin | 424/524 |
| 2006/0140863 | A1 | 6/2006 | Meinert et al. | |
| 2006/0159771 | A1 * | 7/2006 | Kadrmas | A61K 31/726 424/600 |
| 2006/0235068 | A1 | 10/2006 | Snyder et al. | |
| 2007/0280924 | A1 * | 12/2007 | Daniels et al. | 424/94.61 |

FOREIGN PATENT DOCUMENTS

| | | | |
|---|---|---|---|
| CN | 101132814 | 2/2008 | |
| DE | 10255601 | 4/2004 | |
| EP | 1132065 | 9/2001 | |
| EP | 1 752 152 | 2/2007 | |
| JP | 2002-514470 | 5/2002 | |
| JP | WO 2006062233 A1 * | 6/2006 | ........... A61K 31/185 |
| JP | 2008-522953 | 3/2008 | |
| WO | 86/02548 | 5/1986 | |
| WO | 99-58159 | 11/1999 | |
| WO | 99/58159 | 11/1999 | |
| WO | 03/043548 | 5/2003 | |
| WO | WO03057259 | 7/2003 | |
| WO | WO2004035091 | 4/2004 | |
| WO | WO 2006062233 A1 * | 6/2006 | |
| WO | WO2006062233 A1 | 6/2006 | |
| WO | WO2010060018 | 5/2010 | |

OTHER PUBLICATIONS

Syringe Selection Guide (www.harvadappartus.com).*
Needle gauge comparison chart (en.wikipedia.org/wiki/Needle_gauge_comparison_chart).*
Syringe Selection Guide (www.harvardappartus.com).*
Needle gauge comparison chart (e.wikipedia.org/wiki/Needle_gauge_comparison_chart).*
Oberstein et al., Heavy trypan blue staining of epiretinal membranes: an alternative to infracyanine green, Br J Ophthalmol., 91(7):955-7 (2007).
http://ecatalog.alcon.com/pi/BSSplus25.
Ünlü et al., "Gentian violet solution for staining the anterior capsule," J. Cataract Refract Surg., 26:1228-1232 (2000).
Enaida et al., The Journal of Retinal and Vitreous Diseases, 2006, 631-636.
Foster et al., The Journal of Retinal and Vitreous Diseases, 2002, 106-108.
Hisatomi et al., Archives of Opthalmology, 2006,514-519.
Ueno et al., The Journal of Retinal and Vitreous Diseases, 2007, 499-504.
Office Action, CN 2012082001176990, Aug. 23, 2012, with English Translation.

(Continued)

*Primary Examiner* — Michah-Paul Young
(74) *Attorney, Agent, or Firm* — Kagan Binder, PLLC

(57) ABSTRACT

The invention relates to a water-based biocompatible non-cytotoxic preparation for the selective staining of internal limiting membrane (ILM) and/or epiretinal membranes (ERM) in the human or animal eye, and to a kit containing said water-based preparation according to the invention.

14 Claims, No Drawings

(56) References Cited

OTHER PUBLICATIONS

Notice of Reasons for Refusal, JP 2011-541226, Oct. 30, 2012.
English Translation of Third Office Action from State Intellectual Property Office of the People's Republic of China, CN Patent Application No. 200980151548.3.
Oberstein et al., "Heavy trypan blue staining of epiretinal membranes: an alternative to infracyanine green," Br J Opthalmol 2007; 91:955-957.
Chakrabarti et al., "Vital. Dyes for Chromovitrectomy: Colours for the Vitreoretinal Surgeon!!!", 174-179, Jun. 2008.
Costa et al., "Vital dyes and light sources for chromovitrectomy: comparative assessment of osmolarity, pH and spectrophotometry," IOVS Papers in Press, 1-20, Aug. 8, 2008.
Da Mata et al, "Indocyanine Green-assisted Peeling of the Retinal Internal Limiting Membrane during Vitrectomy Surgery for Macular Hole Repair," Opthalmology, vol. 108, No. 7, Jul. 2001, 1187-1192.
Foroutan, "Density Dependence of the Viscosity and Excess Volume of Aqueous Solutions of Polyvinylpyrrolidone," Acta Chin. Slov. 2006, 53, 219-222.
Hillenkamp et al., "Macular function and morphology after peeling of idiopathic epiretinal membrane with and without the assistance of indocyanine green," Br J Ophthalmol 2005, 89, 437-443.
Hillenkamp et al., "Retreatment of full-thickness macular hole: predictive value of optical coherence tomography," Br J Ophthalmol 2007, 91, 1445-1449.
European VitreoRetinal Society a certain philosophy, 2008 EVRS Congress, http://www.evrs.eu/2008-evrs-congress-prague/.
European VitreoRetinal Society a certain philosophy, Staining of Internal Limiting Membrane with Brilliant Blue G Under Air for Macular Hole Surgery video, http://www.evrs.eu/staining-of-internal-limiting-membrane-with-brilliant-blue-g-under-air . . . .
European VitreoRetinal Society a certain philosophy, video transcript.
Horiguchi et al., Effect of Temperature on Electroretinograph Readings During Closed Vitrectormy in Humans, Arch Ophthalmol vol. 109, Aug. 1991, 1127-1129.
Kagimoto et al., "Clinical review of dyes to improve visualization of internal limiting membrane," Opthalmology International, Autumn 2007, vol. 2 No. 3, 89-92.
Kareem, "A volumetric study of aqueous solution of poly (vinyl alcohol) over temperature range 298.15-328.15 K," National Journal of Chemistry, 2006, vol. 22, 250-253, 2-3.
Kirchoff, "Introducing a new dye for vitreoretinal surgery," reprinted from Nov. 2007 issue of Ophthalmology Times Europe, Article Reprint No. 0732.
Lesnik-Oberstein et al., "Improving the staining characteristics of trypan blue in vitreo-retinal surgery," Invest Ophthalmol Vis Sci 2004; 45: E-Abstract 1984.
Lesnik-Oberstein et al., Improving the staining characteristics of trypan blue in vitreo-retinal surgery poster, 2004.
Nishimura et al., "Changes in vitreous concentrations of human hepatocyte growth factor (hHGF) in proliferative diabetic retinopathy: implications for intraocular hHGF production," Clinical Science (2000) 98, 9-14.
Nishimura et al., "Does Precipitation Reduce Tissue Staining by Indocyanine Green Dye Solutions?" Jpon J Ophthalmol 47, 18-21 (2003).
Rinkoff et al., "Temperature-depdenent light damage to the retina" abstract, Am J Ophthalmol. Oct. 15, 1986; 102(4): 452-462.
Rodrigues et al., "Intravitreal Staining of the Internal Limiting Membrane Using Indocyanine Green in the Treatment of Macular Holes," Ophthalmologica 2005; 219:251-262.
Rodrigues et al., "Mechanisms of Intravitreal Toxicity of Indocyanine Green Dye: Implications for Chromovitrectomy," Retina the Journal of Retinal and Vitreous Diseases 2007, vol. 27 No. 7, 958-970.
Saikia et al., "Safety of Indocyanine Green in an Ex Vivo Porcine Retinal Model," Investigative Ophthalmology & Visual Science, Nov. 2006, vol. 47, No. 11, 4998-5003.
Schmidt EVRS 2008 Congress Program.
Schmidt EVRS 2008 Congress Video.
Schmidt EVRS 2008 Congress Video Transcript.
Snyder et al., "Optical Rotations, Refractive Indices, and Densities of Dextran Solutions," Journal of Research of the National Bureau of Standards, vol. 53, No. 3, Sep. 1954, research paper 2525, 131-137.
Stalmans et al., "Toxic Effect of Indocyanine Green on Retinal Pigment Epithelium Related to Osmotic Effects of the Solvent," American Journal of Ophthalmology, vol. 134, No. 2, 282-285.
Vote et al., "Trypan Blue-Assisted Vitrectomy," Retina the Journal of Retinal and Vitreous Diseases, 2004, vol. 24, No. 5, 736-738.

* cited by examiner

DYE SOLUTION

FIELD OF THE INVENTION

The invention relates to a water-based biocompatible preparation for the selective staining of internal limiting membrane (ILM) and/or of epiretinal membranes (ERM) in the human or animal eye, and to a kit containing said water-based biocompatible preparation according to the invention.

BACKGROUND OF THE INVENTION

Disorders of the eye, such as cataract, glaucoma, age-related macular degeneration and diabetes-related retinopathy as well as retinal changes and retinal detachments are increasing, partially owing to higher life expectancy. To treat these and other eye disorders a vitrectomy is often indicated, during which it must be ensured that damage to the retina is minimal. One precautionary measure consists in removing the internal limiting membrane (ILM) and any epiretinal membranes from the retina during the vitrectomy in order to relieve the assumed intravitreal tensile forces on the macula. This is achieved by peeling the membranes away from the retina using forceps. For the surgeon, it is necessary to be able to distinguish as accurately as possible between the retina and the membrane to be peeled away. To this end, the membranes to be peeled away should be made visible by means of staining as specifically as possible. Dyes suitable for staining have to meet many criteria. They must be biocompatible and non-toxic and must not damage the cells; they should be water-soluble, should stain as specifically as possible and should be easily flushed out again. Dyes and methods for staining the said membranes have already been described, but they are not yet completely satisfactory.

Thus, U.S. Pat. No. 7,014,991 describes a method of staining ocular structures in the human eye, wherein the staining takes place by injection of the dye indigotindisulfonate into the appropriate tissue. However, indigotindisulfonate is cytotoxic.

Other dyes, such as Brilliant Blue G, Brilliant Blue R, Patent Blue V or methylene blue, have also been proposed for use in the eye.

During vitrectomy or surgical intervention, the eye socket is flushed with a flushing solution. Now, one problem with the dye solutions known hitherto consists in the fact that the dye solution is dispersed, diluted and flushed out by the flushing solution. This has several disadvantages. On the one hand, the surgeon's view is clouded if the flushing solution is coloured. On the other hand, more dye solution is needed than would be required only for staining the membrane.

In order to overcome this disadvantage it has already been proposed to add a thickener, such as e.g. hyaluronic acid, to the dye solution, which increases the viscosity of the dye solution. The increase in viscosity is intended to reduce the transfer of the dye into the flushing solution as a result of decreased mobility, i.e. through steric hindering, so that more of the dye reaches the area of the membrane to be stained. However, the high viscosity of the dye solution means that it is now difficult for the dye to transfer out of this on to the membrane, so that again the need for dye solution is greater than the amount that would be required only for staining the membrane.

The object of the invention was therefore to provide a preparation which can specifically stain membranes, and in particular can selectively stain the membranes to be removed, such as the internal limiting membrane (ILM) and/or epiretinal membranes (EMR), in the human or animal eye, which can be applied readily, migrates to the membrane immediately after application and disperses there without staining the flushing solution too strongly. In addition, a preparation is to be provided which leads to neither local irritations nor damage to the retina, is not cytotoxic but is well tolerated.

This object is achieved by a preparation as defined in the claims, particularly in claim 1.

The subclaims contain advantageous developments.

DETAILED DESCRIPTION OF THE INVENTION

Surprisingly, it has been found that a preparation that contains at least one dye selected from triphenylmethane dyes and/or azo dyes and/or cyanine dyes and/or natural dyes such as anthocyans and anthocyanidines allows an effective and selective staining of the ILM and/or EMR if the density of the preparation is adjusted to a range of 1.01 $g/cm^3$ to 1.5 $g/cm^3$, preferably 1.01 $g/cm^3$ to 1.3 $g/cm^3$.

It has been found that, when a dye solution with increased density compared to water is injected into the area of the eye socket in the context of a surgical treatment on the eye, it sinks, as a result of which rapid mixing with the flushing solution is avoided, and after sinking, it disperses on and stains the membrane. As a result, the dye is prevented from being flushed away too rapidly with the flushing solution and also from clouding the field of vision.

The preparation according to the invention is based on water as the solvent, other solvents optionally also being contained in minor proportions provided that they can be mixed homogeneously with water and are biologically compatible. Suitable here are mono- and polyhydric alcohols as also used in the medical field. If an additional solvent is used, this is particularly preferably a glycol or glycerol. Mixtures of the said solvents are also suitable. If a solvent is added to the water, this should be used in a proportion of no more than 20 wt. %, more preferably no more than 10 wt. %. The preparation is preferably an isotonic solution.

Apart from water as the solvent and the dye, which is specified in more detail below, the preparation according to the invention contains as an essential component an agent that adjusts the density. The density-adjusting agent must be biologically compatible, non-toxic and homogeneously miscible with water, optionally after adding a small amount of a solubilising agent such as alcohol, so that a clear, transparent solution is formed. In addition, it must be compatible with the dye, i.e. it must not impair the solubility of the dye to any significant extent. In adjusting the preparation, the osmolarity must also be considered in order to avoid causing osmosis-related damage to the tissue. The osmolarity should be within a range of 280-330 mosmol/l, preferably 300 mosmol/l.

Water-compatible fluids the density of which is greater than the density of water are therefore suitable. One advantageous agent for increasing the density is heavy water, $D_2O$, which can be used to adjust the density value to the desired range. Heavy water is distinguished by excellent compatibility. It is tolerated by eukaryotes up to a concentration of 20% in water and does not lead to any irritation in the area of application. It is miscible with water in any concentration, has no tendency to settle or separate and exhibits no discernible differences from water in terms of solubility. The proportion of heavy water in the preparation can be adjusted such that the desired density value of 1.01 $g/cm^3$ to 1.5 $g/cm^3$, preferably of 1.01 $g/cm^3$ to 1.3 $g/cm^3$, is achieved.

The suitable amount, which also depends on the other ingredients, can be found through simple tests or calculations. If heavy water is the density-adjusting agent, it is used preferably in an amount of 5-20%. The production of the preparation using heavy water is also very simple and can take place simply by mixing because of the good miscibility of the two components. From water, heavy water and dye, therefore, a permanently stable preparation which is highly suitable for the purpose of selectively staining membranes can be produced simply and rapidly.

Another agent that can be used to adjust the density is a di- or polysaccharide. Polysaccharides are suitable for increasing the density and are readily available. In addition, they are toxicologically harmless and biologically compatible. In this context, polysaccharides are intended to mean molecules built up from more than two, preferably more than 5, particularly preferably more than 10 saccharide units. Although in general mono- and disaccharides can increase the density, according to the invention only non-reducing disaccharides are used to increase the density. The use of monosaccharides and reducing disaccharides can lead to undesirable effects, for example they can be cytotoxic in the amount needed to increase the density. Non-reducing disaccharides that are suitable according to the invention are sucrose or trehalose. Soluble starch derivatives, such as hydroxyethyl starch and dextran, can be mentioned as suitable polysaccharides. Those substances which are neutral, have no reducing effect and do not decompose in an aqueous solution are suitable as polysaccharides.

Other agents for adjusting the density are neutral polymers such as polyethers, polyvinyl alcohol, polyesters, polyacrylic acid copolymers, polyvinyl pyrrolidone.

Combinations of the above agents are also highly suitable to adjust the density of the preparation according to the invention, e.g. a combination of heavy water and one or more polysaccharides.

The amount of heavy water and/or additional or other density-adjusting agents is selected such that the density of the finished preparation is in the required range of 1.01 g/cm³ to 1.5 g/cm³, preferably 1.01 g/cm³ to 1.3 g/cm³. The density of the preparation can be determined by any common method, as generally known to the person skilled in the art.

It has been shown that increasing the density to 1.01 g/cm³ already has the desired effect, i.e. that the dye solution rapidly sinks downwards after application into the eye socket and can then disperse there on the membrane. This results in a selective staining of the membrane without impairing the surgeon's view. A difference in density of less than 0.01 g/cm³ based on water is no longer sufficient to allow the dye preparation to sink in a targeted manner. In this case, the sinking takes place as slowly as with the preparations of the prior art and leads to the problems mentioned above. If the density of the preparation is greater than 1.5 g/cm³, damage can occur to the very sensitive retina as a result of the density.

Another important component of the preparation according to the invention is the dye. As the dye it is possible to use those compounds that are capable of staining the ILM and/or EMR specifically and in a targeted manner, so that the membrane is distinguished optically from the retina. In addition, the dye must be soluble in the water or the mixture of water and another solvent. It must be neither toxic, particularly cytotoxic, nor damaging to cells, and must not cause damage to the retina or develop toxic effects through light reactions, e.g. ICG or trypan blue. In addition, it should have good tinctorial power in order to be able to keep the amount of the dyes small.

Dyes from the group of the triphenylmethane dyes, such as Brilliant Blue G, Brilliant Blue R, Brilliant Blue FCF, Patent Blue V, Bromophenol Blue, Lissamine Green SF, Lissamine Green G, Fast Green, Methyl Green, Acid Brilliant Green, Coomassie Violet R 200, rose aniline; from the group of the azo and diazo dyes, such as Orange G, Ponceau 2R, Chromotrope 6 R, Ponceau 6 R, tartrazine, azophloxine, Ponceau B, Evans Blue, Chicago Blue; from the group of the cyanine dyes, such as 3,3'-diethylthiacyanine iodide, 3,3'-diethylthiacarbocyanine iodide, 3,3'-diethyl-9-methylthiacarbocyanine iodide, 1,1'-diethyl-4,4'-cyanine iodide and/or from the group of the natural dyes, such as orcein, lawsone, indigotin, canthaxanthin, haematoxylin, indigo carmine and/or anthocyans and anthocyanidines as well as mixtures thereof, i.e. mixtures of several members of one of the above groups and members of different groups, have proved advantageous.

Brilliant Blue G, Brilliant Blue R, Brilliant Blue FCF, Patent Blue V, Methyl Green, Coomassie Violet R 200, Bromophenol Blue and/or Chicago Blue are preferably used. Among the triphenylmethane dyes, Brilliant Blue G, Coomassie Violet R 200 and Chicago Blue are particularly preferred. Among the brilliant blue dyes, Brilliant Blue G is preferred on account of its particularly good tinctorial power. It can be used in a concentration of less than 0.3 g/l. Even this low concentration leads to sufficient selective staining of ILM and/or EMR. Other suitable dyes are Lissamine Green SF, Lissamine Green G, Fast Green, Acid Brilliant Green, Orange G, Ponceau 2R, Chromotrope 6 R, Ponceau 6 R, tartrazine, azophloxine, Ponceau B, Chicago Blue, Evans Blue, 3,3'-diethylthiacyanine iodide, 3,3'-diethylthiacarbocyanine iodide, 3,3'-diethyl-9-methylthiacarbocyanine iodide, 1,1'-diethyl-4,4'-cyanine iodide, orcein, lawsone, indigotin, canthaxanthin, haematoxylin, indigo carmine and various anthocyans.

To improve the advantageous properties of the preparation according to the invention further, a viscosity-adjusting agent can also be added to the preparation. It has been shown that the addition of an agent that increases the viscosity of the preparation according to the invention can bring about an improvement in cohesivity, so that the advantages obtained with the preparation according to the invention are further reinforced. The applied preparation, which sinks more rapidly owing to its higher density, is dispersed even less in the flushing solution, since it is held together until it hits the membrane owing to its increased viscosity. However, since an advantageous effect is already achieved by adjusting the density, the viscosity does not have to be increased so strongly that it leads to problems like those that exist in the prior art. Even a small increase in viscosity means that the drops leaving the applicator form a more stable unit and thus are less readily dilutable, which prevents the dye embedded in the preparation from being flushed out. Thus, the dye is released only at the point of application by capillary effects on to the membrane, which is stained as a result. In this way, the dye can be brought to the membrane in a targeted manner.

One or more from the following group can be used as viscosity-regulating, biocompatible agents, i.e. agents which adjust the viscosity: polyethers, polyvinyl alcohol, polyesters, polyacrylic acid copolymers, polyvinyl pyrrolidone and other polymers, polyhydric alcohols such as glycerol, propylene glycol, butylene glycol, water-soluble cellulose derivatives such as methylcellulose, xanthan gum, starch, hyaluronic acid and their respective derivatives, chondroitin sulfate and sodium sulfate. As the viscosity-regulating agent it is also possible to use those which increase not only the viscosity but at the same time also the density. In this case it is important to ensure that the two parameters, i.e. both the viscosity and the density, are within the desired range. In other words, a density-influencing and viscosity-regulating agent must not be used in an amount such that the finished preparation then has a density of more than 1.5 g/cm$^3$. The suitable amounts can be readily determined by the person skilled in the art using routine tests, however, and the corresponding values adjusted in the preparation.

Particularly suitable as viscosity-regulating agents are those that have a certain affinity to the dye used according to the invention and are distinguished by high spreadability. Surprisingly, it has been found that butylene glycol is an agent with which the viscosity can be regulated and which leads to good spreadability. An addition of butylene glycol can therefore ensure that the applied preparation sinks downwards and, as soon as it has reached the membrane, it spreads out there and rapidly stains the membrane. Without being tied to a theory, this is explained by the fact that, on the one hand, butylene glycol has an affinity to membranes and, on the other hand, owing to lipophilic groups, it adsorbs the dye well. When the preparation containing butylene glycol and dye reaches the membrane, the butylene glycol ensures that the dye can be rapidly dispersed on the membrane.

The viscosity of the preparation according to the invention is preferably adjusted such that the shear viscosity at 25° C. and a shear rate of 10 s$^{-1}$ is in a range of 1 to 500 mPas. Preferably the shear viscosity at 25° C. and a shear rate of 10 s$^{-1}$ is adjusted to a range of 50 to 275 mPas. The adjustment of the viscosity can be achieved with the above-mentioned viscosity-regulating agents. If the viscosity, under the measurement conditions stated, is in a range of 1 to 500 mPas, the effects achieved with the preparation according to the invention are significantly reinforced. The preparation containing the selectively staining dye sinks rapidly without the dye being washed out with the flushing solution to any significant degree. The dye is therefore released only at the point of application by means of capillary effects on to the membrane, which is stained as a result. If the viscosity under the measurement conditions stated is lower than 1 mPas, the effect of the rapid settling of the preparation according to the invention cannot be additionally reinforced. The possibility exists that at least part of the dye is removed with the flushing solution before staining the membrane and thus is no longer available for staining the membrane. If, on the other hand, the dynamic viscosity at 25° C. and a shear rate of 10 s$^{-1}$ is above 500 mPas, the viscosity of the preparation is so high that the dye cannot be released optimally from the droplets that form. The ability of the dye preparation to spread, which causes rapid, homogeneous staining of the membrane, is therefore significantly reduced. The membrane is not wetted optimally with the dye preparation and therefore is not dyed as clearly. A particularly good staining result is achieved if the dynamic viscosity at 25° C. and a shear rate of 10 s$^{-1}$ is in a range of 50 to 275 mPas.

It has been found that, when administering dye solutions into the eye, problems may occur. If the dye solution is administered with the syringes generally used, the pressure achieved during injection is too high, so that the dye can pass behind the retina.

The problem is solved according to the invention by using syringes in which cannula diameter, the ratio of barrel diameter to cannula diameter and the aspect ratio are adjusted in such a way as to avoid damage. According to the invention, syringes in which the cannula diameter is very small are preferably used in order to minimise damage in the eye. Furthermore, the barrel diameter is adjusted to the cannula diameter in such a way that the occurrence of a Venturi effect is largely avoided. In other words, in the syringe provided for administration, the diameter of the barrel must also be as small as possible so that the ratio of barrel diameter to cannula diameter is in the range of from 10 to 2:1 to 0.2, preferably 20:1 to 4:1, particularly preferably 16:1 to 8:1. In addition, the syringe barrels should have an aspect ratio, i.e. ratio of barrel length to barrel diameter, in a range of 15 to 5:1.

The invention therefore also provides a kit, which comprises a syringe with barrel and cannula containing a dye preparation for the selective staining of the internal limiting membrane and/or of epiretinal membranes in the human or animal eye, wherein the ratio of barrel diameter to cannula diameter is in the range of 10-2:1-0.2, preferably 20:1 to 4:1, particularly preferably 16:1 to 8:1. The ratio of barrel length to barrel diameter is preferably in a range of 15 to 5:1. As a component which is essential to the invention, the kit thus comprises a syringe whose barrel diameter is adjusted to the diameter of the cannula. It has been found that, with a smaller ratio of the diameter, no pressure can build up in the internal chamber upstream of the cannula, so that a uniform application, i.e. an application with uniform pressure and constant velocity of the preparation according to the invention, is guaranteed. The kit preferably contains a dye preparation according to the invention as described above.

For the kit or its syringe, preferably a cannula with 19 to 27 gauge, particularly preferably 23 or 25 gauge, is used. Cannulae with 19 to 27 gauge are suitable for injections into the eye. Their outlet aperture is so small that they do not leave any significant damage at the injection site, but yet they are large enough to apply the preparation according to the invention in the eye at an adequate velocity. If the barrel of the syringe is appropriately adapted in its diameter, a build-up of pressure is avoided inside the syringe or cannula, which would bring the preparation into the eye under too great a pressure during injection so that the preparation would be dispersed beyond the point of application, e.g. behind the retina. In terms of the desired application, cannulae with 20, 23, 25 or 27 gauge, in particular those with 23 or 25 gauge, have proved particularly good. In a preferred embodiment a cannula of this type is used together with a syringe with a barrel diameter of 3 to 10 mm. Particularly preferred are cannulae with 23 or 25 gauge if the dynamic viscosity of the preparation at 25° C. and a shear rate of 10$^{-1}$ is in a range of 1 to 500 mPas. In this precise case, the interplay between cannula and preparation is so good that, at a sufficiently rapid rate, a sufficiently large amount of the preparation according to the invention can be deposited uniformly at the point of application without an explosive ejection of the preparation from the cannula occurring as a result of pressure build-up. The preparation is thus prevented from being injected behind the desired point of application, as a result of which an optimum staining of the membrane can be achieved.

The preparations according to the invention described above and the syringes provided to administer them allow the targeted staining of membranes—ILM and/or ERM—in the eye. Depending on the dye used, it is possible to stain either only one type of membrane, i.e. only ILM or only ERM, or to stain both types. In one embodiment the preparation according to the invention can be used to cause negative dyeing of the epiretinal membranes so that these can then be removed. In this embodiment a solution of a dye, e.g. Brilliant Blue G, is used, which selectively dyes the ILM but not the ERM. In this way, the undyed membrane (ERM) can be distinguished from the dyed membrane (ILM) and can thus be readily removed.

The invention is further explained by the following examples, which describe dye solutions with increased density and the production thereof, without restricting it thereto.

Example 1

0.025 g Brilliant Blue G, 5 g sucrose, 0.19 g disodium hydrogen phosphate, 0.03 g sodium dihydrogen phosphate and 0.82 g sodium chloride are accurately weighed and topped up to 100 g with distilled water. The raw materials are treated in a glass flask for 1 h at a maximum of 60° C., resulting in a homogeneous solution with a dye concentration of 0.25 g/l and a density of 1.023 g/cm$^3$.

Example 2

0.025 g Brilliant Blue G, 5 g trehalose, 0.19 g disodium hydrogen phosphate, 0.03 g sodium dihydrogen phosphate and 0.82 g sodium chloride are weighed accurately and topped up to 100 g with distilled water. The raw materials are treated in a glass flask for 1 h at a maximum of 60° C., resulting in a homogeneous solution with a dye concentration of 0.25 g/l and a density of 1.023 g/cm$^3$.

Example 3

0.025 g Brilliant Blue G, 0.19 g disodium hydrogen phosphate, 0.03 g sodium dihydrogen phosphate and 0.82 g sodium chloride are weighed accurately and topped up to 100 g with a mixture of distilled water and D$_2$O. The raw materials are treated in a glass flask for 1 h at a maximum of 60° C., resulting in a homogeneous solution with a dye concentration of 0.25 g/l and a density of 1.018 g/cm$^3$.

Example 4

Dye+Glycerol 0.025 g Brilliant Blue G, 0.19 g disodium hydrogen phosphate, 0.03 g sodium dihydrogen phosphate and 0.82 g sodium chloride are weighed accurately and topped up with a mixture of distilled water and 10% glycerol. The raw materials are treated in a glass flask for 1 h at a maximum of 60° C., resulting in a homogeneous solution with a dye concentration of 0.25 g/l and a density of 1.027 g/cm$^3$.

Example 5

Using the method as described in Examples 1 to 4, a dye solution with the following composition was produced

| Substance | Set weight in g | Actual weight in g |
| --- | --- | --- |
| Polyvinyl pyrrolidone | 6 | 6.0067 |
| Brilliant Blue G | 0.0125 | 0.0125 |
| Na$_2$HPO$_4$*2H$_2$O | 0.095 | 0.0950 |
| NaH$_2$PO$_4$*2H$_2$O | 0.015 | 0.0159 |
| NaCl | 0.41 | 0.4100 |
| Water | to 50 g | to 50 g |

A homogeneous solution was obtained with a density of 1.028 g/cm$^3$ and a viscosity of 7.38 mPas.

Example 6

Using the method as described in Examples 1 to 4, a dye solution with the following composition was produced

| Substance | Set weight in g | Actual weight in g |
| --- | --- | --- |
| Methylcellulose E 10M (2 wt. %) | 25 | 24.9986 |
| Brilliant Blue G | 0.0125 | 0.0125 |
| Na$_2$HPO$_4$*2H$_2$O | 0.095 | 0.0956 |
| NaH$_2$PO$_4$*2H$_2$O | 0.015 | 0.0151 |
| NaCl | 0.41 | 0.4099 |
| Water | to 50 g | to 50 g |

A homogeneous solution was obtained with a density of 1.007 g/cm$^3$ and a viscosity of 142.79 mPas.

The dye solutions produced in Examples 1 to 6 were used for staining the internal limiting membrane in the human or animal eye. It was found that all six solutions could be applied very well and sank immediately after application and stained the ILM. With the same amount of dye, the colouring was even more intense than with a Brilliant Blue G solution, as known from DE 10255601, which was applied for comparison.

The invention claimed is:

1. An intravetreous water-based, biocompatible eye membrane dye solution, comprising at least one dye selected from the group consisting of triphenylmethane dyes, azo dyes, natural dyes, and mixtures thereof and, wherein the intravetreous solution has a density in the range of 1.01 g/cm$^3$ to 1.5 g/cm$^3$, wherein the eye membrane dye solution has a dynamic viscosity in the range of 1 to 500 mPas, at 25° C. and a shear rate of 10 s$^{-1}$, wherein the dye solution contains an agent for adjusting the density and wherein said at least one dye stains the internal limiting membrane or the epiretinal membrane so that the membranes are distinguished optically from the retina, with the proviso that monosaccharides or reducing disaccharides are not used for adjusting the density.

2. The eye membrane dye solution according to claim 1, wherein the dye is Brilliant Blue G or Coomassie Violet R200.

3. The eye membrane dye solution according to claim 2, wherein the concentration of the Brilliant Blue G in the eye membrane dye solution is up to 0.3 g/l.

4. The eye membrane dye solution according to claim 1 for use as a dye for a negative representation of epiretinal membranes.

5. The eye membrane dye solution according to claim 1, wherein the osmolarity of the solution is in the range of 280-330 mosmol/l.

6. A kit comprising a syringe with barrel with a diameter of 3 to 10 mm and cannula with 19 to 27 gauge and the water-based eye membrane dye solution according to claim 1, wherein the dye is Brilliant Blue G and the concentration of the Brilliant Blue G in the eye membrane dye solution is up to 0.3 g/l, and wherein the ratio of barrel diameter to cannula diameter is in a range of 10:0.2 to 2:1.

7. The kit according to claim 6, wherein the ratio of barrel length to barrel diameter is in a range of 15:1 to 5:1.

8. The eye membrane dye solution according to claim 1, wherein the dye is selected from the group consisting of azo dyes, natural dyes, and mixtures thereof.

9. An intravetreous water-based, biocompatible eye membrane dye solution, comprising at least one dye selected from the group consisting of triphenylmethane dyes, azo dyes, natural dyes, and mixtures thereof and an agent that adjusts the density of the preparation selected from the group consisting of polyether, polyvinyl alcohol, polyester, polyacrylic acid copolymer and polyvinyl pyrrolidone, wherein the intravetreous solution has a density in the range of 1.01 g/cm$^3$ to 1.5 g/cm$^3$, wherein the eye membrane dye solution has a dynamic viscosity in the range of 1 to 500 mPas, at 25° C. and a shear rate of 10 s$^{-1}$, and wherein said at least one dye stains the internal limiting membrane or the epiretinal membrane so that the membranes are distinguished optically from the retina.

10. The eye membrane dye solution according to claim 9, wherein the dye is Brilliant Blue G or Coomassie Violet R200.

11. The eye membrane dye solution according to claim 10, wherein the concentration of the Brilliant Blue G in the eye membrane dye solution is up to 0.3 g/l.

12. The eye membrane dye solution according to claim 9 for use as a dye for a negative representation of epiretinal membranes.

13. The eye membrane dye solution according to claim 9, wherein the osmolarity of the solution is in the range of 280-330 mosmol/l.

14. The eye membrane dye solution according to claim 9, wherein the dye is selected from the group consisting of azo dyes, natural dyes, and mixtures thereof.

\* \* \* \* \*

UNITED STATES PATENT AND TRADEMARK OFFICE
CERTIFICATE OF CORRECTION

PATENT NO. : 9,498,547 B2  
APPLICATION NO. : 12/990427  
DATED : November 22, 2016  
INVENTOR(S) : Christian Lingenfelder et al.

Page 1 of 1

It is certified that error appears in the above-identified patent and that said Letters Patent is hereby corrected as shown below:

In the Claims

Column 8  
Line 60 "Brilliant Blue Gin" should be -- Brilliant Blue G in --

Column 9  
Line 19 "Brilliant Blue Gin" should be -- Brilliant Blue G in --

Signed and Sealed this  
Eighteenth Day of April, 2017

Michelle K. Lee  
*Director of the United States Patent and Trademark Office*